US00PP19330P3

(12) United States Plant Patent

Maillard et al.

(10) Patent No.: US PP19,330 P3

(45) Date of Patent: Oct. 14, 2008

(54) NECTARINE TREE NAMED 'NECTACHIEF'

(50) Latin Name: ***Prunus persica* (L.) Batsch-Yellow Nectarine**
Varietal Denomination: NECTACHIEF

(75) Inventors: Laurence Maillard, Elne (FR); Arsene Maillard, Elne (FR)

(73) Assignee: S.A.R.L. Agro Selection Fruits, Elne (FR)

( * ) Notice: Subject to any disclaimer, the term of this patent is extended or adjusted under 35 U.S.C. 154(b) by 167 days.

(21) Appl. No.: 11/434,906

(22) Filed: May 17, 2006

(65) Prior Publication Data

US 2006/0265793 P1 Nov. 23, 2006

(51) Int. Cl.
*A01H 5/00* (2006.01)

(52) U.S. Cl. ..... Plt./190

(58) Field of Classification Search ..... Plt./190
See application file for complete search history.

*Primary Examiner*—Annette H Para

(74) *Attorney, Agent, or Firm*—Westerman, Hattori, Daniels & Adrian, LLP.

(57) ABSTRACT

A new and distinct variety of nectarine tree, denominated 'Nectachief', has an evenness of maturity, a very sure, regular and large quantity of productivity, a long lifetime before and after harvest, and an aromatic semi sweet taste.

2 Drawing Sheets

Botanical classification: *Prunus persica* (L.) Batsch-Yellow Nectarine.

BACKGROUND OF THE VARIETY

The present invention relates to a new and distinct variety of *Prunus persica* (L.) Batsch yellow nectarine tree. This tree, named 'Nectachief', produces very long lifetime, good eating quality, semi-clingstone to clingstone fruit for fresh market in July in the 66-Pyrénées-Orientales departement-France. Contrast is made to 'Zaitabo' nectarines, standard varieties, for reliable description. 'Nectachief' is a promising candidate for commercial success in that it has an evenness of maturity, and produces regular fruits in large quantity and with a high productivity. It was chosen because of fruit lifetime before and after harvest, and because of its aromatic semi sweet taste.

ORIGIN OF THE VARIETY

'Nectachief' nectarine tree originated in a cultivated area of the south of France, in the 66-Pyrénées-Orientales departement-France where it was tested. This place is under a Mediterranean climate in a temperate area characterized by irregular and low precipitation with drought in summer, high temperatures all year long. The 'Nectachief' variety was obtained by seedling. The male parent was 'Zaitabo' nectarine tree and the female parent was 'Armking' (U.S. Plant Pat. No. 2,943) nectarine tree. 'Nectachief' was provisionally designated and tested as 01.23.01 NJ and is registered at the Official Catalogue of the Agriculture Ministry of the French Republic Dec. 29, 2004, under number 1016557. It was obtained from open-pollination sowing of hybrid and is propagated by grafting. It has been determined to have unique tree and fruit characteristics making it worthy for commercial fresh fruit production. There are no known effects of this standard rootstock on this scion cultivar. Asexually propagated plants remained true to the original tree and all characteristics of the tree and the fruit were transmitted. The plant was reproduced asexually by us in Les Régalines, Route d'Alenya, La Prade de Mousseillous, 66200 ELNE, Pyrénées-Orientales, France.

SUMMARY OF THE VARIETY

The new and distinct variety of nectarine tree blooms in March at Perpignan in the Pyrénées-Orientales departement, France. More particularly, it blooms at the same time as 'Nectaross' or 'Maillarmate', and 3 days after "Zaitabo" between $7^{th}$ and $21^{st}$ of March.

The first fruit of 'Nectachief' ripens in early July 6 days after 'Zaitabo'. More particularly, it approximately ripens between June $4^{th}$ and $13^{th}$.

DESCRIPTION OF THE DRAWINGS

In the accompanying drawing, which are as nearly true as it is reasonably possible to make in a colour illustration of this type.

DETAILED BOTANICAL DESCRIPTION

Figure 1:
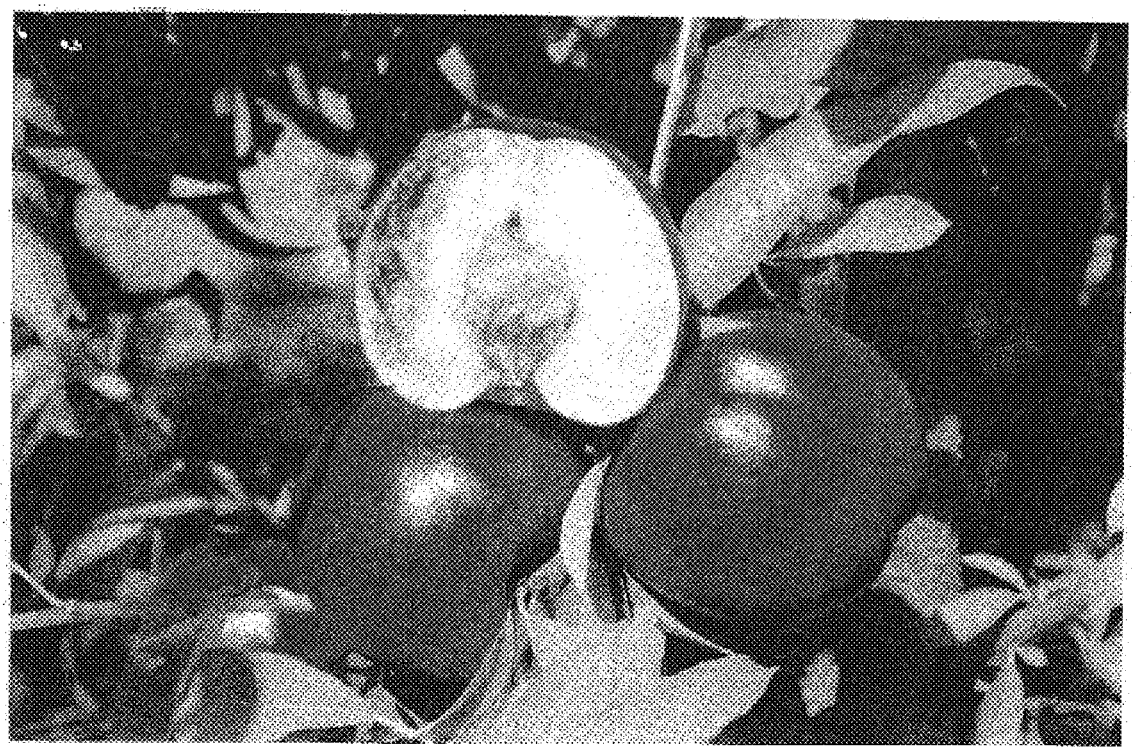
FIG. 1 is a colour photograph which shows the flesh of the fruit of the new variety 'Nectachief'.
Figure 2:
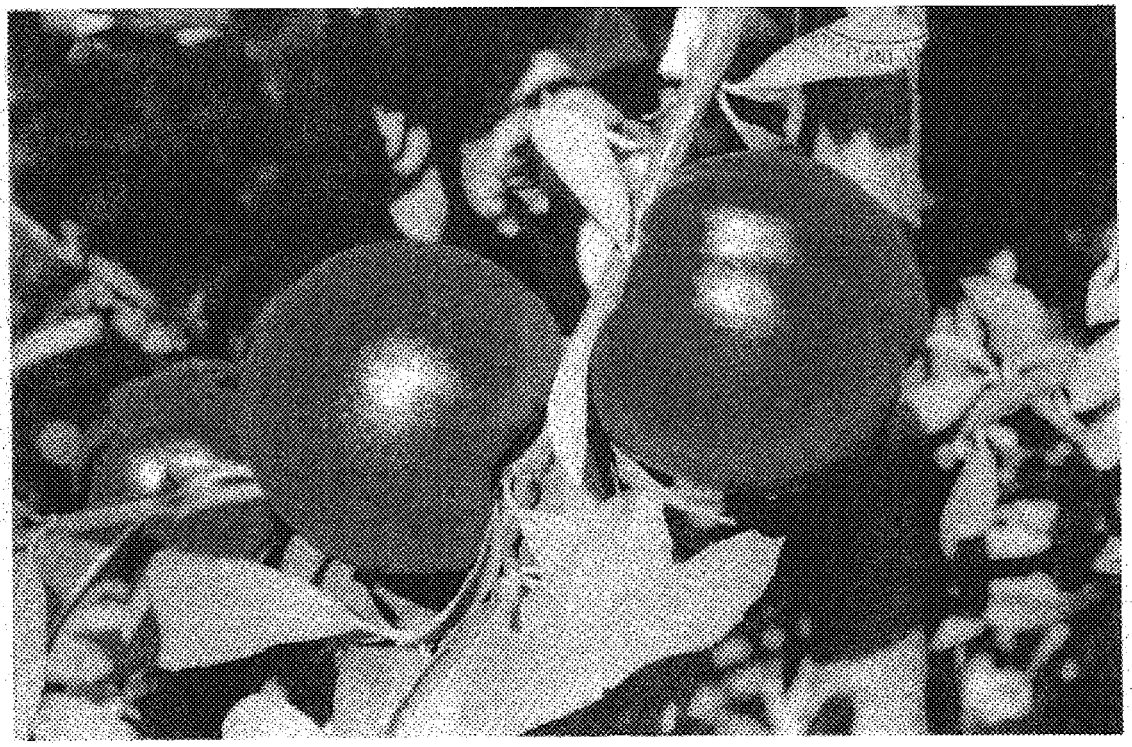
FIG. 2 is a colour photograph which shows a typical specimen of the fruit of the new variety 'Nectachief'.

The tree, flowers, and fruit may vary in slight detail due to variations in soil type, cultural practices, and climatic condition. The potential for commercial production of fresh fruit by 'Nectachief' is high, due to its fruit early ripening, and fruit evenness of maturity.

Trees are vigorous and medium stature half-standing in a semi-spread to semi-upright out aspect. The flowering shoot is present excluding brushwood side away from sun. Flowering begins early in springtime. The type of flower is showy with relative medium to large petal size. Petals are pink. One or two leaf glands are present on petiole and one or two on leaf. Leaf glands are reniform. Time of maturity for consumption is early. The fruit flesh is yellow and its skin has a large and homogeneous bright dark red blush. The stone is medium size and the flesh is adherent.

Compared to 'Zaitabo' variety, 'Nectachief' has an older time of maturity, 6 to 7 days later. The evenness of maturity is higher, and picking can be done within 10 days to 2 weeks instead of three weeks. Number of flowers is bigger, approximately more than 40 to 45 flowers per square meter instead of 15 to 20 flowers for 'Zaitabo'. Fruits can be harvested in 2 times. The flesh tastes more aromatic even if the texture is similar. The stone is not splitted like in 'Zaitabo' variety.

DETAILED DESCRIPTION

Referring more specifically to the pomological details of this new and distinct variety of nectarine tree, the following has been observed during the second fruiting season under the ecological condition prevailing at the orchards located near the town of Elne, in the Pyrénées-Orientales departement, France. All observations have been done on rootstock cultivar. The rootstock was a 'Franc Inra Montclar®' tree. All major color code designations are by reference to The R.H.S. Color Chart (Fourth Edition) provided by The Royal Horticultural Society of Great Britain.

Tree

Size:

*Generally.*—Considered medium to large as compared to other common commercial nectarine cultivars ripening in the middle season of maturity. The tree size the first year was approximately 280 cm. The tree was pruned during each following dormant season to a height of approximately 250 cm. Current season shoots growth could reach 80 cm. So the tree size from the second year (second and next years) reached a final height of 330 cm with current season shoots length comprised.

Spread: Approximately 150 cm with a cylindrical shape. The whole orchard was oriented to a central leader organisation, with tree lines spaced of 4.0 meters and trees spaced of 1.0 meter in a same tree line. As a result, the orchard contains 2500 trees by hectare.

Vigour: Considered vigorous.

Productivity: Very Productive. Fruit set is spaced by thinning to develop the remaining fruit into the desired market sized fruit. The number of the fruit set varies with the prevailing climatic conditions, and cultural practices employed during the bloom period, and is therefore not distinctive of the present variety.

Bearer: Very regular. Fruit set has been heavy during the years of observation and thinning of 1 fruit on 3 was necessary every year during the past 5 years.

Form: The 'Nectachief' variety has naturally a semi-spread to semi-upright shape.

Density: Considered dense.

Hardiness: The present tree was grown and evaluated in France. The variety appears to be hardy under typical central Pyrénées-Orientales departement climatic conditions. Experimentations on different sites with winter chilling requirement comprised between 350 and 1200 hours showed a good behavior of the tree in all cases. Ascertained temperatures as low as −10 degrees Celsius caused no damages to the tree. The tree was also very resistant to frosty springtime weather.

TRUNK

Diameter: Approximately between 4.0 and 8.0 cm in diameter when measured at a distance of approximately 30 cm above the soil level.

Bark texture: Considered moderately rough, with numerous folds of papery scarfskin being present.

Lenticels: Numerous lenticels are present. The lenticels range in size from approximately 0.3 to 0.5 cm in width, and from 0.1 to 0.2 cm in height.

Lenticel colour: The outside of lenticels has a silver-grey color (RHS Grey 201 D to RHS Black 202 D), whereas the inside is considered brown (RHS Greyed Orange 166B-C-D).

Bark colouration: The bark has a silver-grey color (RHS Grey 201 C to RHS Black 202 C) as well as a brown-grey color (RHS Grey Brown 199 A-B-C).

BRANCHES

Size: Mature branches as well as current season shoots are medium to thick for the variety.

Diameter: Average as compared to other nectarine varieties. The current season shoots have a diameter from 4.0 to 7.0 millimeters, and branches of trees have a diameter comprised between 15.0 and 20.0 millimeters.

Surface texture: Average, wood which is several years old has no furrowed appearance.

Crotch angles: Primary branches are considered variable, but the crotch angles are generally between 50 and 60 degrees from the horizontal axis. This particular characteristic is not considered distinctive of the variety, however.

Current season shoots:

*Surface texture.*—Substantially glabrous.

Internode length: Generally 20.0 to 25.0 millimeters.

Colour of mature branches: Medium brown (RHS Grey Brown 199 A) with fine grey streaks (RHS Grey Group 201D).

Current seasons shoots:

*Colour.*—The color of new shoot tips is considered a light yellow green (RHS Yellow Green 144 A-B) on lower part of new shoot tips, whereas the upper part is colored in reddish brown (RHS Greyed Purple Group 183 B-C).

LEAVES

Size: Considered medium to large for the species. Leaf measurements have been taken from vigorous, upright, current-season growth at approximately mid-shoot. The ratio leaf length/leaf width is around 3.6 to 3.8.

Leaf length: Approximately 160 to 195 millimeters with petiole.

Leaf width: Approximately 45 to 55 millimeters.

Leaf base shape: Slightly oblique relative to the leaf longitudinal axis.

Leaf form: Lanceolate.

Leaf tip form: Acuminate.

Leaf colour:

*Upper leaf surface.*—Dark Green (RHS Green 137 A).

*Lower surface.*—Medium Green (RHS Green 137 B to 137 C).

Leaf texture: Smooth and glabrous.

Leaf colour: Green.

Leaf venation: Pinnately veined.

Mid-vein:

*Colour.*—Light yellow green (RHS Yellow Green 144 D to 144 C).

Leaf margins: Slightly undulating.

Form: Considered slightly dentate.

Uniformity: Leaves are isolated or grouped by 2 or 3. In this last case, it is found one leaf of normal size with one or two smaller leaves (size-reduction of 50% and more).

Leaf petioles:

*Size.*—Considered medium.

*Length.*—About 10.0 to about 15.0 mm.

*Diameter.*—About 1.8 to about 2.3 mm.

*Colour.*—Light yellow green (RHS Yellow Green 144 D to 144 C).

Leaf glands:

*Size.*—Considered medium.

*Number.*—Generally 1 to 2 glands on the petiole and 1 to 2 glands on the leaf.

*Type.*—Reniform.

*Colour.*—On young leaves, leaf glands color is considered a pale green (RHS Green 144 B). On older leaves, leaf glands color turn to a dark brown (RHS Grey Brown 199 A to 199 B).

Leaf stipules:

*Generally.*—No leaf stipules were observed. But as seen in the characteristic relative to the leaves uniformity, it is possible to find leaves by groups of 2 or 3, with a normal-size leaf and smaller ones.

FLOWERS

Flower buds:

*Generally.*—At pre-floral stage of development, the floral buds are conic in form with a round tip. Their form is evolving until blooming, with variables dimensions. Just before blooming, floral buds are approximately 10.0 millimeters wide and approximately 18.0 millimeters long.

Flower buds:

*Colour.*—This characteristic is dependent upon the proximity to bloom. At pre-floral stage of development, the bottom of the flowers buds, formed by sepals, is of purple-brown color (RHS Greyed Purple 183 A); the corolla, formed by petals, is generally of pink color (RHS Red Purple 65 B-C). Petals color shows an evolution until the end of flowering. The buds are considered hardy under typical central Pyrénées Orientales departement climatic conditions.

Hardiness: No winter injury was noted during the last several years of evaluation in the central Pyrénées Orientales departement, with winter temperatures as low as −10 degrees Celsius in December or January. The current variety has not been intentionally subjected to drought or heat stress, but the variety showed a very good resistance in orchard to temperatures up to 42 degrees Celsius with an average temperature between 28 and 30 degrees Celsius during 3 weeks in summer.

Date of bloom: Generally early March. The first bloom, observed on Feb. 26, 2002, was exceptionally early. Second and third bloom took place respectively on Mar. 11, 2003 and Mar. 6, 2004.

Blooming time: Considered early-season in relative comparison to other commercial nectarine cultivars grown in the Pyrénées-Orientales departement, France. The date of full bloom is observed on March, more particularly between Mar. $7^{th}$ and $21^{st}$. The date of bloom varies slightly with climatic conditions and cultural practices.

Duration of bloom: Approximately 15 days. This characteristic varies slightly with the prevailing climatic conditions.

Flower type: The variety is considered to have a showy type flower.

Flower size: Considered medium to large. Flower diameter at full bloom is approximately 34.0 to about 40.0 millimeters.

Bloom quantity: Considered very abundant, approximately from 40 to 45 flowers per meter.

Flower bud frequency: Generally 2 flower buds appear per node, occasionally 1.

Petal size:

*Generally.*—Considered medium to large for the species.

Length: Generally about 19.0 millimeters.

Width: Generally about 19.0 millimeters.

Petal form: Rounded.

Petal count: Nearly always 5.

Petal texture: Smooth and glabrous.

Petal colour: Pale Pink (RHS Red Purple 69 B-C) when young, darkening with advancing senescence.

Fragrance: Slight.

Petal claw:

*Form.*—The claw is considered to have a conic form with a slightly rounded extremity.

*Length.*—Approximately 5.0 to 6.0 millimeters.

*Width.*—Approximately 4.0 to 5.0 millimeters.

Petal margins: Generally slightly undulated.

Petal apex:

*Generally.*—The petal apices are generally entire at the tip, dome-shaped.

Flower pedicel:

*Length.*—Considered medium-long and having an average length of approximately 3.0 to 5.0 millimeters.

*Diameter.*—Considered average, approximately 2.0 millimeters.

*Colour.*—A medium brown (RHS Grey Brown N199 B to C).

Floral nectarines:

*Colour.*—A flat golden orange (approximately RHS Greyed Red 178 C-B).

Calyx:

*Internal surface texture.*—Smooth and glabrous.

*Color.*—The outer surface of the calyx is considered of Purple-brown (RHS Greyed Purple 183 A) color.

Sepals:

*Surface texture.*—The outer surface has a short, fine pubescent texture.

*Size.*—Average.

*Colour.*—A flat Red (approximately RHS Greyed Red 178 A). Average number of stamens per flower: Approximately 40 stamens per flower.

Anthers:

*Generally.*—Average in length.

*Color.*—Red to orange-red color (approximately RHS Greyed Purple 178 A Group). Anthers are becoming yellow at maturity.

Pollen production: Pollen is abundant, and has a yellow color (Approximately RHS Yellow Orange 17 B-C). The present variety is considered self fruitful (self-pollinating).

Filaments:

*Size.*—Variable in length, approximately 11.0 to 16.0 millimeters in length. In all cases filament's length is superior or equal to pistil's length.

Color: Considered light pink (approximately RHS Red Purple 62 C-D) to darker pink (RHS Red Purple 73 A-B) with advancing senescence.

Pistil:

*Number.*—Usually 1.

*Generally.*—Average in size.

*Length.*—Approximately 16.0 to 19.0 millimeters including the ovary; Smaller or equal to filament's length.

*Colour.*—Considered a very pale green (varying from RHS Yellow Green 150 D Group to RHS Yellow Green 151 D Group).

*Surface texture.*—The variety has a glabrous pistil.

FRUIT

Maturity when described: Firm ripe condition (shipping ripe).

Date of first picking: Jul. 3, 2003. The picking generally occurs between July $4^{th}$ and $13^{th}$. The date of harvest varies slightly with the prevailing climatic conditions.

Date of last picking: Jul. 13, 2003, only 2 harvests in 10 days were necessary.

Size:

*Generally.*—Considered large, and uniform.

Average cheek diameter: Approximately 75.0 to 79.0 millimeters.

Average axial diameter: Approximately 66.0 to 74.0 millimeters.

Typical weight: Approximately between 150.0 and 200.0 grams. This characteristic is high dependent upon the prevailing cultural practices, and therefore is not particularly distinctive of the variety.

Fruit form:

*Generally.*—Round to slightly oblate. The fruit is generally uniform in symmetry, viewed from pistil end.

Fruit suture: Very shallow and smooth, extending from the base to the apex. No apparent callousing or stitching exists along the suture line.

Suture:

*Colour.*—This has generally a color similar to the whole fruit color, a bright dark red (RHS Red Group 46 A-B) blush on a yellowish orange (RHS Yellow Orange 23 A-B) background, the blush covering from 90 to 100 percent of the fruit skin surface.

Ventral surface:

*Form.*—Smooth.

Apex: Non-prominent, slightly depressed, very small.

Base: Shallow.

Stem cavity: Average depth of the stem cavity is about 0.7 cm. Average width is about 1.5 cm.

Fruit skin:

*Thickness.*—Considered very thick and strong, and very tenacious to the flesh to tenacious to the flesh depending on stage of maturity.

*Texture.*—Glabrous.

*Taste.*—Semi-sweet.

*Tendency to crack.*—None observed.

Colour:

*Blush colour.*—This blush colour is generally a bright dark red (RHS Red Group 46 A-B) blush. The red blush covers more than 90% of the fruit skin surface. The percentage of the blush on the fruit skin surface can vary, and is generally dependant upon the prevailing conditions under which the fruit was grown.

*Ground colour.*—Yellow Orange (RHS Yellow Orange 23 A-B).

Fruit stem: Medium in length, approximately between 7.0 and 8.0 millimeters.

Diameter: Approximately 4.0 millimeters.

Colour: Pale green (RHS Yellow Green 145A to 145 B), darkening with maturity.

Flesh:

*Ripens.*—Very evenly, homogeneous, long shelf-life of the fruit.

*Texture.*—Very firm, very dense, juicy at harvest maturity stage.

*Fibers.*—No fibers.

*Aroma.*—Pronounced.

*Eating quality.*—Considered very good and spicy.

*Flavor.*—Considered semi-sweet. The Brix is superior to 13.0 degrees. Acidity is comprised between 6 and 9 meq/100 ml. The flavor is considered spicy. The flesh is juicy.

*Juice.*—Very juicy at complete maturity.

*Brix.*—Generally superior to 13.0 degrees. This characteristic varies slightly with the number of fruit per tree; prevailing cultural practices; and the surrounding climatic conditions.

*Flesh colour.*—Generally Yellow Orange (RHS Yellow Orange 16 B) with a slight red pigmentation (RHS Red 45 A-45 B).

STONE

Type: Semi-clingstone to Clingstone.

Size: Considered medium for the variety.

Length: Approximately between 28.0 and 32.0 millimeters.

Width: Approximately between 21.0 and 25.0 millimeters.

Diameter: Approximately between 16.0 and 28.0 millimeters.

Form: Elliptic.

Base: Straight.

Apex:

*Shape.*—The stone apex has a small sharp tip.

Stone cavity: Considered medium size, with an elliptic-form and dimensions corresponding to stone's dimensions.

Stone surface:

*Surface texture.*—The pit is transversely furrowed on its entire surface. Furrows are more pronounced toward the apex. The stone is pitted toward the base. Relief is prominent generally and present basally.

*Ridges.*—The surface texture is generally characterized by more prominent ridges along the ventral edges and is more prominent at the apical tip.

Ventral edge:

*Width.*—Considered small to medium, and having a dimension of approximately 2.0 millimeters at mid-suture.

Dorsal edge:

*Shape.*—Grooved.

Stone colour: The color of the dry stone is generally considered a light orange brown (RHS Greyed Orange 176 C) to reddish brown (RHS Greyed Red 178 B).

Tendency to split: Split is absent or very low, depending on climatic conditions between blooming period and stone hardening.

Kernel:

*Size.*—The kernel is considered medium.

*Length.*—About 16.0 millimeters.

*Width.*—About 10.0 millimeters.

*Thickness.*—About 3.0 millimeters.

*Form.*—Considered oblate and elliptic.

*Pellicle.*—Pubescent but difficult to see.

*Colour.*—The kernel skin is brown-orange (RHS Greyed Orange 167 D) with darker brown-orange streaks (RHS Greyen Orange N167 B). The almond is cream-white (RHS Orange Chite 159 D). The kernel and its embryo are mature at the time of fruit maturity.

Use: The subject variety 'Nectachief' is considered to be a nectarine tree of the early season of maturity, and which produces fruit that are considered very firm, attractively coloured. Fruits are excellent for uncooked consumption, crunchy or at full maturity. Due to their flesh quality, firmness and density, they can also be commercialized as $4^{th}$ range product (packed fruit or fruit in bags for example). And they are also useful for both local and very long distance shipping.

Keeping quality: Excellent. Fruit stayed a little more than one week on tree before harvest and then, has stored well more than 4 weeks after harvest at 2.0 degree Celsius. They have a slow maturation and a long shelf life both on the tree after growth completion and after harvesting without alteration.

Shipping quality: Considered very good. The fruit of the new nectarine variety showed minimal bruising of the flesh or skin damage after being subjected to normal harvesting and packing procedures. Its resistance to handling during harvest and packing and its long shelf life without alteration after harvest easily permit 3 to 4 weeks shipping at 2 degrees Celsius.

Resistance to insects and disease: No particular susceptibilities were noted. Under our climatic conditions, favourable to powdery mildew, and with few treatments, the present variety has not been shown to be very sensitive to powdery mildew, or conservation diseases and decay due to its thick and strong skin. No bacteriostatic substances were applied, and no symptom was observed. Although the new variety of nectarine tree possesses the described characteristics when grown under the ecological conditions prevailing near the town of Elne, France, it should be understood that variations of the usual magnitude and characteristics incident to changes in growing conditions, fertilization, pruning, pest control and horticultural management are to be expected.

What is claimed is:

1. A new and distinct nectarine tree variety as illustrated and described, characterized by an evenness of maturity, a very sure, regular and large quantity of productivity, a long lifetime before and after harvest, and an aromatic semi sweet taste.

* * * * *

UNITED STATES PATENT AND TRADEMARK OFFICE

CERTIFICATE OF CORRECTION

PATENT NO. : PP19,330 P3
APPLICATION NO. : 11/434906
DATED : October 14, 2008
INVENTOR(S) : Laurence Maillard et al.

It is certified that error appears in the above-identified patent and that said Letters Patent is hereby corrected as shown below:

On the title page:
Insert

--(30) Foreign Application Data

May 18, 2005 (QZ)..... 2005-0908--

Signed and Sealed this
Eleventh Day of March, 2014

Michelle K. Lee

Michelle K. Lee
*Deputy Director of the United States Patent and Trademark Office*